United States Patent
Soens et al.

(10) Patent No.: US 10,736,638 B2
(45) Date of Patent: Aug. 11, 2020

(54) METHOD OF APPLYING HEMOSTATIC OR TISSUE HEALING AGENT TO WET SURFACES

(71) Applicant: BOSTON SCIENTIFIC SCIMED, INC., Maple Grove, MN (US)

(72) Inventors: Meghan Elizabeth Soens, Paris (FR); Andrew Schaubhut, Stow, MA (US); Caroline Riedel, Weston, MA (US); Sergey Kantsevoy, Maple Grove, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 309 days.

(21) Appl. No.: 15/280,345

(22) Filed: Sep. 29, 2016

(65) Prior Publication Data
US 2017/0100128 A1 Apr. 13, 2017

Related U.S. Application Data

(60) Provisional application No. 62/238,321, filed on Oct. 7, 2015.

(51) Int. Cl.
*A61B 17/12* (2006.01)
*A61B 17/00* (2006.01)

(52) U.S. Cl.
CPC .. *A61B 17/12181* (2013.01); *A61B 17/00234* (2013.01); *A61B 17/00491* (2013.01); *A61B 2017/00818* (2013.01); *A61B 2017/00884* (2013.01); *A61B 2017/00893* (2013.01); *A61B 2017/00951* (2013.01); *A61B 2017/12004* (2013.01); *A61B 2017/1205* (2013.01)

(58) Field of Classification Search
CPC ........ A61B 17/12181; A61B 17/00234; A61B 17/00491; A61B 2017/1205; A61B 2017/00951; A61B 2017/00884; A61B 2017/12004
See application file for complete search history.

(56) References Cited

U.S. PATENT DOCUMENTS

| 5,395,383 | A | 3/1995 | Adams et al. |
| 5,514,158 | A | 5/1996 | Kanesaka |
| 7,985,197 | B2 * | 7/2011 | Maeda ............... A61B 17/3468 604/60 |
| 8,052,660 | B2 | 11/2011 | Yamamoto et al. |

(Continued)

FOREIGN PATENT DOCUMENTS

| WO | 97/021383 | 6/1997 |
| WO | 2004/103187 | 12/2004 |

*Primary Examiner* — Bradley J Osinski
(74) *Attorney, Agent, or Firm* — Fay Kaplun & Marcin, LLP

(57) ABSTRACT

A device for applying a tissue healing agent includes an insertion member extending longitudinally from a proximal end to a distal end and including a channel extending therethrough, a delivery element including a first surface and a second surface opposing one another, the delivery element movable between a closed configuration, in which the delivery element is compressed to be received within the channel, and an open configuration, in which the delivery element is substantially planar, and a first tissue healing agent formed in a sheet configuration and disposed on the first surface of the delivery element.

11 Claims, 3 Drawing Sheets

(56) References Cited

U.S. PATENT DOCUMENTS

| | | |
|---|---|---|
| 8,465,516 B2 | 6/2013 | Pavenik et al. |
| 2003/0236573 A1 | 12/2003 | Douglas et al. |
| 2004/0167572 A1* | 8/2004 | Roth ................... C08L 27/18 606/219 |
| 2005/0019262 A1 | 1/2005 | Chernomorsky et al. |
| 2007/0082021 A1* | 4/2007 | Bates ............... A61B 17/12022 424/423 |
| 2010/0280547 A1 | 11/2010 | D'Alessio et al. |
| 2011/0166550 A1 | 7/2011 | Aleaxander et al. |
| 2012/0143296 A1 | 6/2012 | Pianca et al. |
| 2012/0253115 A1 | 10/2012 | Erin |
| 2013/0096610 A1* | 4/2013 | Pins ................. A61B 17/12099 606/228 |

\* cited by examiner

METHOD OF APPLYING HEMOSTATIC OR TISSUE HEALING AGENT TO WET SURFACES

PRIORITY CLAIM

This application claims priority to U.S. Provisional Patent Application Ser. No. 62/238,321 filed Oct. 7, 2015; the disclosure of which is incorporated herewith by reference.

BACKGROUND

To treat wounds, ulcer beds, perforations and surgical bleeds, physicians may apply materials such as, for example, gels, particulates, sheets, tissue scaffolds or polymers, to wet tissue surfaces. With the increasing use of tissue resection procedures, there is a clinical need to provide methods to manage complications, including bleeding, defect beds and perforations, and promote healing. For example, a tissue healing agent may need to be applied to achieve hemostasis at an active bleed site where the source can be approximately identified for, for example, post resection defects, ulcer defects or tumor bleeds. Currently, bleeds and/or tissue defects may be treated by delivering a gel or power like substance through an existing or modified endoscopic catheter. However, gel material may not naturally sufficiently adhere to wet tissue and may drip away from its intended site. In some cases, the delivery of powder material may be wide-spread and somewhat uncontrolled. In addition, there is no common method for applying or delivering tissue and/or polymer sheets to tissue.

SUMMARY

The present disclosure relates to a device for applying a tissue healing agent, comprising an insertion member extending longitudinally from a proximal end to a distal end and including a channel extending therethrough, a delivery element including a first surface and a second surface opposing one another, the delivery element movable between a closed configuration, in which the delivery element is compressed to be received within the channel, and an open configuration, in which the delivery element is substantially planar, and a first tissue healing agent formed in a sheet configuration and disposed on the first surface of the delivery element.

In an embodiment, the delivery element may be biased toward the open configuration and is constrained in the closed configuration via an interior surface of the channel.

In an embodiment, the delivery element, in the closed configuration, may be rolled upon itself to be received within the channel.

In an embodiment, a perimeter of the delivery element may include a curvature at a proximal end thereof so that, when the delivery element is moved proximally toward the insertion member, in the open configuration, contact between the proximal end of the delivery element and the distal end of the insertion member urges the delivery element toward the closed configuration.

In an embodiment, the device may further comprise a control member attached to the delivery element for moving the delivery element between the open and the closed configurations.

In an embodiment, the delivery element may be moved between the open and closed configurations by rotating the control member about a longitudinal axis thereof.

In an embodiment, the tissue healing agent may have adhesive properties.

In an embodiment, the tissue healing agent may include at least one of a steroid, a polymer, a polyglycolic acid, a fibrin glue and a tissue cell matrix sheet.

In an embodiment, the device may further comprise a release mechanism for releasing the first tissue healing agent from the first surface of the delivery element.

In an embodiment, the release mechanism may include an element slidable along the first surface between the first surface and the first tissue healing agent.

In an embodiment, the release mechanism may include an element extendable away from the first surface to release the first tissue healing agent therefrom.

In an embodiment, the device may further comprise a second tissue healing agent formed in a sheet configuration and disposed on the second surface of the delivery element.

The present disclosure also relates to a device for applying a tissue healing agent, comprising an insertion member extending longitudinally from a proximal end to a distal end and including a channel extending therethrough, a delivery element including a first surface and a second surface opposing one another, the delivery element movable between a closed configuration, in which the delivery element is compressed to be received within the channel, and an open configuration, in which the delivery element is substantially planar, a control member connected to the delivery element and extending proximally therefrom to move the delivery element between the open and closed configurations, a tissue healing agent formed in a sheet configuration and disposed on the first surface of the delivery element, and a release mechanism movable coupled to the delivery element for releasing the tissue healing agent therefrom.

In an embodiment, the release mechanism may include an element slidable along the first surface between the first surface and the first tissue healing agent.

In an embodiment, the release mechanism may include an element extendable away from the first surface to release the first tissue healing agent therefrom.

The present disclosure also relates to a method for applying a tissue healing agent to a target tissue, comprising inserting an insertion member into a living body to a target tissue to be treated, the insertion member extending longitudinally from a proximal end to a distal end and including a channel extending therethrough, a delivery element housed in the insertion member in a closed configuration in which the delivery element is compressed, moving the delivery element distally relative to the insertion member to an open configuration in which the delivery element expands to be substantially planar, the delivery element including first and second opposing surfaces, the first surface including a tissue healing agent formed in a sheet configuration and disposed thereon, and pressing the tissue healing against the target tissue to be treated.

BRIEF DESCRIPTION

DETAILED DESCRIPTION

Figure 1:
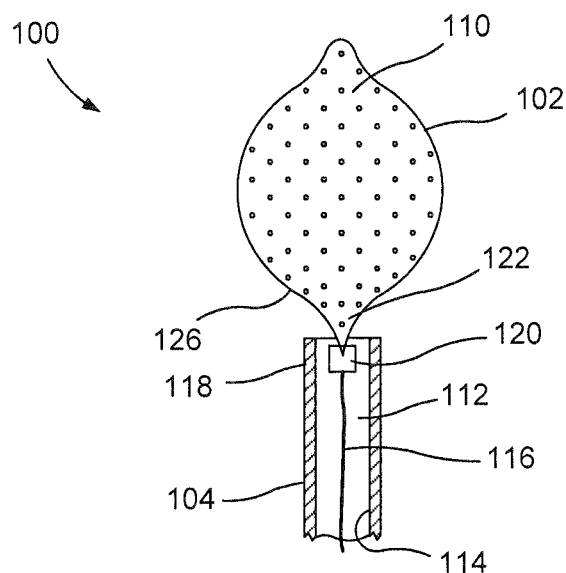
FIG. 1 shows a partially cross-sectional view of a device according to an exemplary embodiment of the present disclosure.

The present disclosure may be further understood with reference to the appended drawings and the following description, wherein like elements are referred to with the same reference numerals. The present disclosure relates to devices and methods for applying a tissue healing agent and/or hemostatic agent to tissue and, in particular, relates to applying a tissue healing and/or hemostatic agent during an endoscopic procedure. Exemplary embodiments of the present disclosure describe a device including a delivery element on which a tissue healing agent may be disposed. The delivery element may be, for example, a flexible paddle-shaped element movable between a closed configuration, in which the delivery element is rolled or folded so that the delivery element is insertable through, for example, an insertion catheter, and an open configuration, in which the flexible paddle is unrolled or unfolded so that the tissue healing agent may be applied to, for example, tissue along a gastrointestinal (GI) wall. It will be understood by those of skill in the art that the term "tissue healing agent", as used herein also includes a hemostatic agent. It should be noted that the terms "proximal" and "distal", as used herein, are intended to refer to a direction toward (proximal) and away from (distal) a user of the device (e.g., physician).

Figure 2:
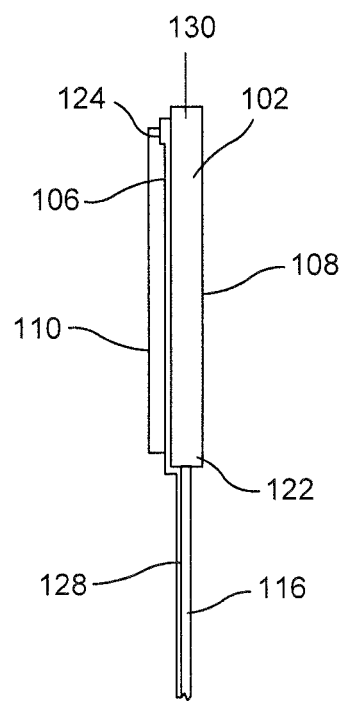
FIG. 2 shows a cross-sectional view of a delivery element of the device of FIG. 1, along a line A-A.

As shown in FIGS. 1 and 2, a device 100 comprises a flexible delivery element 102 on which a tissue healing agent 110 is disposed in a sheet configuration. The delivery element 102 is passed through an insertion member 104 such as, for example, an endoscopic catheter, via a control member 116 which moves the delivery element 102 longitudinally relative to the insertion member 104. The delivery element 102 may, in an open configuration, be expanded to expose a substantially planar or curved element that is sufficiently flexible to be moved between a closed configuration and an open configuration and which has sufficient flexibility to permit it to conform to a shape of tissue against which it is pressed. In the closed configuration, the delivery element 102 is rolled, folded or otherwise compressed (e.g., reduced in size and/or diameter) so that the delivery element 102 is sized and shaped to be passed through a channel 112 of the insertion member 104. In the open configuration, the delivery element 102 is unrolled, unfolded or otherwise radially expanded (e.g., to a configuration in which a radial extent of the delivery element is greater than an inner diameter of the channel 112). For example, the delivery element 102 may be biased toward the open configuration so that, when the delivery element 102 is extended longitudinally beyond the distal end of the channel 112, the delivery element 102 is freed from the constraint of the inner surface of the channel 112 and reverts under its natural bias to the open configuration. As those skilled in the art will understand, the delivery element may, in the open configuration be substantially planar or curved along a shape selected to correspond to a shape of a surface of the tissue to be treated to deliver the tissue healing agent 110 to target tissue such as, for example, a tissue surrounding and/or including a tissue defect, perforation or other bleed.

The insertion member 104 extends longitudinally from a proximal end (not shown) to a distal end 118 and includes the channel 112 extending longitudinally therethrough. In one example, the insertion member 104 may be a flexible endoscopic catheter. The insertion member 104 may be, however, any element through which the delivery element 102 may be inserted to the site of target tissue to be treated and is preferably sufficiently flexible to be inserted to sites in the body which may be accessed along a tortuous path such as through a natural body lumen accessed via a natural bodily orifice. An exemplary insertion member 104 is sized and shaped to be inserted through, for example, a working a channel of an endoscope.

The delivery element 102 may, for example, be shaped substantially similarly to a paddle including first and second opposing, generally planar or curved surfaces 106, 108. The delivery element 102 is sufficiently flexible such that the delivery element 102 is movable between the closed configuration and the biased open configuration. The delivery element 102 may, for example, be biased toward the open configuration and maintained in the closed configuration by an interior surface of 114 of the channel 112 of the insertion member 104. Once the delivery element 102 is moved distally past a distal end 118 of the insertion member 104 via the control member 116, however, the delivery element 102 is permitted to revert under its natural bias to the open configuration. In the open configuration, the delivery element 102 remains substantially flexible so that the tissue healing agent 110, which is disposed along one or both of the surfaces 106, 108 thereof in a sheet configuration, may be pressed flush against a tissue surface to be treated. Since the delivery element 102 has some flexibility, the delivery element 102 is capable of contouring to a surface of a tissue wall such as, for example, a surface of the GI tract, similarly to an endoscopic snare or retrieval net which contours to a gastric wall surface.

In one exemplary embodiment, the delivery element 102 may, in the open configuration, have a substantially rounded shape—e.g., a perimeter of the delivery element 102 or a perimeter of a portion of the delivery element may be curved. In particular, proximal edges 126 may be curved so that, when it is desired to remove the delivery element 102 from the living body, the delivery element 102 may be smoothly drawn proximally into the insertion member 104 with the curved proximal edges 126 contacting the distal end 118 of the insertion member 104 urging the delivery element to fold on itself to return from the open configuration to the closed configuration. As the delivery element 102 is drawn further proximally relative to the insertion member 104, the delivery element 102 is received within the insertion member 104 and again constrained in the closed configuration therewithin. As would be understood by those skilled in the art, the delivery element 102 may be structured so that, in the open configuration it assumes any of a variety of shapes and/or sizes for delivering a tissue healing agent 110 to tissue surfaces of a corresponding variety of shapes and sizes.

The control member 116 extends from a distal end 120 connected to a proximal end 122 of the delivery element 102 to a proximal end (not shown) which extends proximally of a proximal end of the insertion member 104 to be accessible to a user of the device 100. Thus, moving the control member 116 longitudinally relative to the insertion member 104 moves the delivery element between the open and closed configurations. The control member 116 may be connected to the delivery element 102 to provide degrees of freedom of movement to the delivery element 102 relative to the control member 116.

The tissue healing agent 110 may be formed in a sheet so that, when disposed along either or both of the first and second surfaces 106, 108 of the delivery element 102, the tissue healing agent 110 substantially covers one or both of the first and second surfaces. The tissue healing agent 110, however, is also preferably sufficiently flexible so that the tissue healing agent 110 during expansion and compression (e.g., rolling) of the delivery element between the open and closed configurations, the tissue healing agent remains in place on the corresponding surface(s) of the delivery element 102. The tissue healing agent 110 may be, for example, a steroid, desiccant, or polymer formed in a sheet configuration to promote tissue healing/hemostasis of a tissue defect. The tissue healing agent 10 may be resorbable such that the tissue healing agent 110 dissolves within the body after a predetermined amount of time. Examples of tissue healing agents 110 include polyglycolic acid, fibrin glue, and tissue cell matrix sheets.

Figure 3:
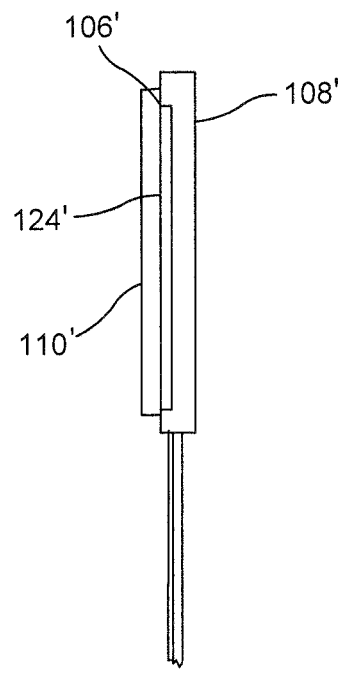
FIG. 3 shows a cross-sectional view of a delivery element of the device of FIG. 1, according to an alternate embodiment of the present disclosure.

In one embodiment, the adhesive properties of the tissue healing agent 110 adheres to tissue with which it is brought into contact and is drawn off of the delivery element 102 as the delivery element 102 is moved away from this tissue. In another embodiment, as shown in FIG. 2, the device 100 further comprises a release element 124 for releasing the tissue healing agent 110 from the delivery element 102. For example, the release element 124 of this embodiment lifts an edge of the tissue healing agent 110 away from the delivery element 102 as the tissue healing agent 110 is pressed against the target tissue. In another example, the release mechanism is slidable along the surface 106, 108 on which the tissue healing agent 110 is disposed, between the proximal end 122 and a distal end 130 thereof, between the first surface 106 and the tissue healing agent 110 disposed thereon to release the tissue healing agent 110. In another example, as shown in FIG. 3, a release element 124' extends along a portion of a length and/or width of a first surface 106' to which a tissue healing agent 110' is disposed so that actuating the release element 124' moves the release element 124' away from the first surface 106' of a delivery element 102' to release the tissue healing agent 110'. Although FIG. 3, shows the tissue healing agent 110' disposed on the first surface 106', a tissue healing agent may also be disposed on a second surface 108' so that the second surface 108' may also include a release element 124'.

The release mechanisms 124 (and the release mechanism 124') may be actuated via an actuator which extends proximally of a proximal end of the insertion member 104 to be accessible to the user of the device 100 (i.e., which remains outside the body when the delivery element is inserted into the body to a target tissue site). The release mechanism 124 may be connected to the actuator via, for example, a control wire 128 which extends from the release mechanism 124 to the actuator along or within the control member 116. The control wire 128 may be longitudinally movable relative to the control member 116 to control a movement of the release mechanism 124 relative to the delivery element 102.

It is noted that although the exemplary embodiment shows and/or describes the tissue healing agent 110 as disposed on the first surface 106, a second sheet of the tissue healing agent 110 may also be disposed on the second surface. In an embodiment in which a second sheet of the tissue healing agent is disposed on the second surface 108 of the delivery element 102, the device 100 may comprise a second release mechanism for releasing the second sheet of the tissue healing agent 110 from the second surface 108 of the delivery element 110.

According to an exemplary method using the device 100, the insertion member 104, with the delivery element 102 housed therein in the closed configuration, is inserted into a living body to the target tissue to be treated via, for example, a working channel of an endoscope inserted through, for example, a body lumen accessed via a naturally occurring bodily orifice. Once the distal end 118 has been positioned proximate the target tissue, the delivery element 102 may be moved to the open configuration via the control member 116. As the delivery element 102 is moved distally past the distal end 118 of the insertion member 104, the delivery element 102 reverts to the biased open configuration in which the delivery element is unrolled or expanded such that the first and second surfaces 106, 108 are substantially planar or curved to approximate a shape of a tissue surface against which it is pressed. The first surface 106, which has the tissue healing agent 110 disposed thereon in a sheet configuration, is then pressed against the target tissue so that the tissue healing agent 110 is applied to the target tissue.

As discussed above, the flexibility of the delivery element 102 permits the delivery element 102 to conform to a shape of a surface of the target tissue to aid in application of the tissue healing agent 110 therein. Where the tissue healing agent 110 is not sufficiently adhesive to disengage from the delivery element 102 upon pressing of the tissue healing agent 110 against the target tissue, a release mechanism 124 may be actuated to release the tissue healing agent 110 from the first surface 106 and onto the target tissue. If the device 100 includes a second sheet of the tissue healing agent 110 on the second surface 108, the second surface 108, with the tissue healing agent 110 disposed thereon, the above-described process may be repeated by pressing the second surface 108 against a second portion of tissue to be treated to apply the tissue healing agent 110 thereon. Similarly, a release mechanism may be actuated to release the second sheet of the tissue healing agent 110 from the second surface 108.

When it is desired to remove the device 100 from the living body, the device 100 is moved to the closed configuration by drawing the delivery element 102 proximally into the insertion member 104. Curved proximal edges 126 of the delivery element 102 contact the distal end 118 of the insertion member 104 to urge the delivery element 102 into the closed configuration. Once the delivery element 102 is drawn into the channel 112 of the insertion member 104 and is in the closed configuration, the device 100 may be removed from the body.

Figure 4:
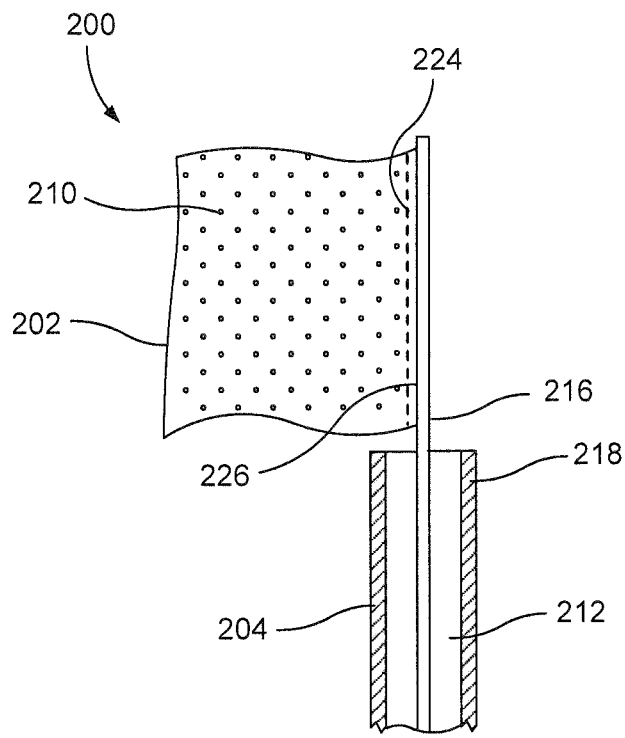
FIG. 4 shows a partially cross-sectional view of a device according to another exemplary embodiment of the present disclosure, in an open configuration.
Figure 5:
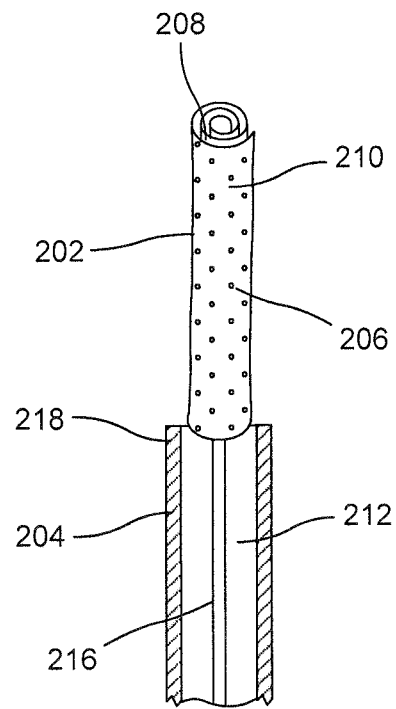
FIG. 5 shows a partially cross-sectional view of the device of FIG. 4, in a closed configuration.

As shown in FIGS. 4 and 5, a device 200 according to another exemplary embodiment of the present disclosure may be substantially similar to the device 100, comprising a delivery element 202 slidably received within a channel 212 of an insertion member 204. Similarly to the device 100, a tissue healing agent 210 is disposed on either or both of the first and second surfaces 206, 208 of the delivery element 202. The delivery element 202, however, is movable between an open configuration, as shown in FIG. 4, and closed configuration, as shown in FIG. 5, via rotation of a control member 216. The delivery element 202 is connected to the control member 216 along a longitudinal side 226 thereof so that, when the control member 216 is rotated in a first direction about a longitudinal axis thereof, the delivery element 202 is wound or rolled about a distal portion of the control member 216 in the closed configuration. When the control member 216 is rotated in a second direction about the longitudinal axis, the delivery element 202 is unrolled to an open configuration to apply the tissue healing agent 210 to a target tissue.

Similarly to the delivery element 102, the delivery element 202 has substantially planar or curved first and second surfaces 206, 208, when the delivery element 202 is in the open configuration. The delivery element 202 is flexible so that, when the control member 216, which is connected to the delivery element 202 to control movement thereof, is rotated about the longitudinal axis in the first direction, the delivery element 202 is rolled about the distal portion of the control member 216 to which the delivery element 202 is connected. Thus, the delivery element 202 may be housed within the channel 212 of the insertion member 204 during insertion and removal of the device 200 into a living body to the target tissue to be treated. In addition, the flexibility of the delivery element 202 allows the delivery element 202 to conform to a shape of a tissue surface against which it is pressed.

The tissue healing agent 210 may be substantially similar to the tissue healing agent 110. In particular, the tissue healing agent 210 is disposed on one of the first and second surfaces 206, 208 in a sheet configuration so that, when the delivery element 202 is rolled into the closed configuration, the tissue healing agent 210 is similarly rolled thereinto. Where the tissue healing agent 210 is disposed on only one of the first and second surface 206, 208, the tissue healing agent 210 may be on the first surface 206, which is positioned so that, when rolled into the closed configuration, faces outward—toward the target tissue.

In use, the insertion member 204 is inserted to the target tissue, with the delivery element 202 therein in the closed configuration, via, for example, a working channel of an endoscope. Once a distal end 218 of the insertion member 204 is positioned proximate the target tissue, the delivery element 202 is moved distally relative to the insertion member 204 until a proximal end 222 of the delivery element 202 is distal the distal end 218. The delivery element 202, in the closed configuration, is pressed against the target tissue and moved from the closed configuration to the open configuration. In particular, the control member 216 is rotated about the longitudinal axis thereof to unroll the delivery element 202 against the target tissue to be treated. In one embodiment, the adhesive properties of the tissue healing agent 210 may cause the sheet of the tissue healing agent 210 to be released from the delivery element 202 as the tissue healing agent 210 is pressed against the target tissue. Alternatively, a release mechanism 224, may be actuated to release the tissue healing agent 210 from the delivery element 210. The release mechanism 224 may be substantially similar to the release mechanism 124 described above in regard to device 100. For example, the release mechanism 224, as shown in broken line in FIG. 4, may cause an edge of the tissue healing agent 210 to lift away from delivery element 202. In another example, the release mechanism 224 may include an element that is slidable across the first surface 206, on which the tissue healing agent 210 is disposed.

Figure 6:
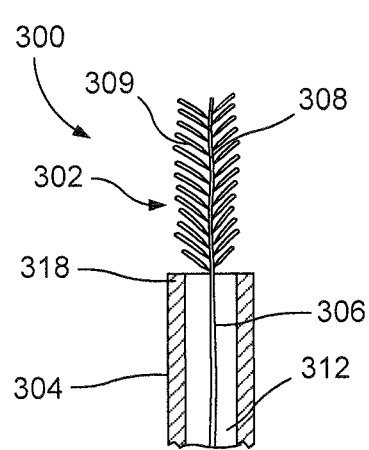
FIG. 6 shows a cross-sectional view of a device according to yet another exemplary embodiment of the present disclosure.
Figure 7:
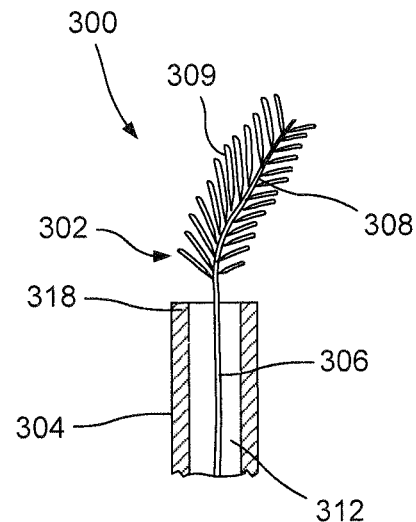
FIG. 7 shows a cross-sectional view of a device according to an alternate embodiment of the present disclosure.

As shown in FIGS. 6 and 7, a device 300 for applying a liquid or gel tissue healing agent according to another exemplary embodiment of the present disclosure may comprise a delivery element 302 slidable through an insertion member 304 to deliver the tissue healing agent to a target tissue. The insertion member 304 may be substantially similar to the insertion members 104, 204 described above in regard to the device 100, 200. The insertion member 304 is insertable through, for example, a working channel to the target tissue. The delivery element 302 may be, for example, a brush including a shaft 306 and a distal portion 309 including bristles 308 thereon. The bristles 308 may trap and hold the tissue healing agent therebetween when the bristles 308 is pre-soaked therein. The brush 302 is then passed through the insertion member 304, distally beyond a distal end 318 thereof, until the bristled distal portion 309 reaches the target tissue to apply the tissue healing agent thereto. The bristled distal portion 309 may be straight relative to the shaft 306, as shown in FIG. 6, or angled, as shown in FIG. 7, so that when extended distally from the insertion member 304, the bristles 308 more easily contact a surface of the target tissue to apply the tissue healing agent thereon. Additional tissue healing gent may be passed through the channel 312 and simply guided and applied via the distal portion 309 to the desired target area. The tissue healing agent may be applied through, for example, a luer lock channel via a syringe or other fluid delivery system (e.g., centrifugal pump).

Figure 8:
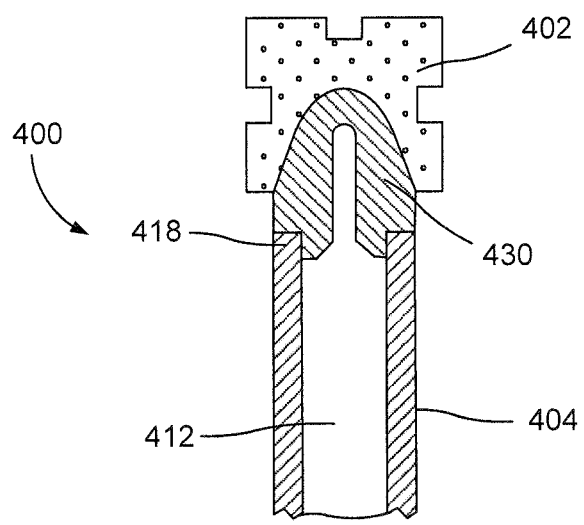
FIG. 8 shows a cross-sectional view of a device according to another exemplary embodiment of the present disclosure.

As shown in FIG. 8, a device 400 for delivering a tissue healing agent to a target tissue according to another exemplary embodiment of the present disclosure comprises a foam applicator 402 connected to a distal end 418 of a longitudinal member 404 via a hard cap 430. The longitudinal member 404 may be, for example, a catheter including a delivery lumen 412 extending longitudinally therethrough. The tissue healing agent may have a substantially liquid or gel-like form so that the tissue healing agent may be passed through the delivery lumen 412 to the foam applicator 402. The cap 430 connecting the foam applicator 402 to the longitudinal member 404 may include one or more openings through which the tissue healing agent may be passed to the foam applicator 402.

The device 400 may be inserted to the target tissue via a working channel of an endoscope. In a further embodiment, the device 400 may further include an insertion member through which the device 400 may be inserted to the target tissue. The insertion member may act as a protective outer lumen in which the foam applicator 402 is housed until it reaches the target tissue.

Variations may be made in the structure and methodology of the present disclosure, without departing from the spirit and the scope of the disclosure. Thus, it is intended that the present disclosure cover the modifications and variations of this disclosure that may be contemplated by a person of skill in the art.

What is claimed is:

1. A device for applying a tissue healing agent, comprising:
    an insertion member extending longitudinally from a proximal end to a distal end and including a channel extending therethrough;
    a delivery element including a first surface and a second surface opposing one another, the delivery element movable between a closed configuration, in which the delivery element is compressed to be received within the channel, and an open configuration, in which the delivery element is substantially planar; and
    a first sheet of a first tissue healing agent disposed on the first surface of the delivery element; and
    a release mechanism for releasing the first sheet of the first tissue healing agent from the first surface of the delivery element, the delivery element being configured to return to the closed configuration after release of the first sheet of the first tissue healing agent therefrom so that the delivery element may be withdrawn into the insertion member for withdrawal from the body, wherein the release mechanism includes an element slidable along the first surface between the first surface and the first sheet of the first tissue healing agent.

2. The device of claim 1, wherein the delivery element is biased toward the open configuration and is constrained in the closed configuration via an interior surface of the channel.

3. The device of claim 1, wherein, in the closed configuration, the delivery element is rolled upon itself to be received within the channel.

4. The device of claim 1, wherein a perimeter of the delivery element includes a curvature at a proximal end thereof so that, when the delivery element is moved proximally toward the insertion member, in the open configuration, contact between the proximal end of the delivery element and the distal end of the insertion member urges the delivery element toward the closed configuration so that the delivery element may be withdrawn into the insertion member for withdrawal from the body.

5. The device of claim 1, further comprising a control member attached to the delivery element for moving the delivery element between the open and the closed configurations.

6. The device of claim 5, wherein the delivery element is moved between the open and closed configurations by rotating the control member about a longitudinal axis thereof.

7. The device of claim 1, wherein the first tissue healing agent has adhesive properties.

8. The device of claim 1, wherein the first tissue healing agent includes at least one of a steroid, a polymer, a polyglycolic acid, a fibrin glue and a tissue cell matrix sheet.

9. The device of claim 1, wherein the release mechanism includes an element extendable away from the first surface to release the first sheet of the first tissue healing agent therefrom.

10. The device of claim 1, further comprising a second sheet of a second tissue healing agent disposed on the second surface of the delivery element.

11. The device of claim 10, wherein the second healing agent includes at least one of a steroid, a polymer, a polyglycolic acid, a fibrin glue and a tissue cell matrix sheet.

* * * * *